(12) United States Patent
Kloster

(10) Patent No.: US 8,990,991 B2
(45) Date of Patent: Mar. 31, 2015

(54) POWER TOOTHBRUSH AND BRUSHHEAD THEREFOR, WITH MULTIPLE MOTION BRUSH MEMBER

(75) Inventor: Tyler Kloster, Snoqualmie, WA (US)

(73) Assignee: Koninklijke Philips N.V., Eindhoven (NL)

(*) Notice: Subject to any disclaimer, the term of this patent is extended or adjusted under 35 U.S.C. 154(b) by 0 days.

(21) Appl. No.: 13/883,866

(22) PCT Filed: Nov. 30, 2011

(86) PCT No.: PCT/IB2011/055387
§ 371 (c)(1),
(2), (4) Date: May 7, 2013

(87) PCT Pub. No.: WO2012/085718
PCT Pub. Date: Jun. 28, 2012

(65) Prior Publication Data
US 2013/0255013 A1  Oct. 3, 2013

Related U.S. Application Data

(60) Provisional application No. 61/424,743, filed on Dec. 20, 2010.

(51) Int. Cl.
*A61C 17/34* (2006.01)
*A46B 7/08* (2006.01)
*A46B 13/02* (2006.01)

(52) U.S. Cl.
CPC ........... *A61C 17/3481* (2013.01); *A61C 17/349* (2013.01)
USPC ................................ 15/22.1; 15/28

(58) Field of Classification Search
CPC .................................... A61C 17/3481
USPC ........................... 15/22.1, 28, 22.2
See application file for complete search history.

(56) References Cited

U.S. PATENT DOCUMENTS

| 3,196,299 | A | * | 7/1965 | Kott | 310/81 |
| 3,284,829 | A | * | 11/1966 | Allen | 15/22.1 |
| 5,033,150 | A | * | 7/1991 | Gross et al. | 15/22.1 |
| 5,867,856 | A | | 2/1999 | Herzog | |
| 7,430,777 | B2 | * | 10/2008 | Scherl | 15/22.1 |
| 2003/0182744 | A1 | | 10/2003 | Fattori et al. | |

(Continued)

FOREIGN PATENT DOCUMENTS

| DE | 102008060696 | * | 6/2010 | A46B 9/04 |
| FR | 2616306 A1 | * | 12/1988 | A46B 7/06 |

(Continued)

OTHER PUBLICATIONS

FR 2616306 A1 (machine translation), 1988.*

*Primary Examiner* — Mark Spisich
*Assistant Examiner* — Andrew A Horton

(57) ABSTRACT

The brushhead (14) includes a neck portion (15) which connects at a proximal end thereof to a handle portion (12) of a power toothbrush (10). At the distal end of the neck portion is a brush member (16, 28) which includes a bristle base plate (18, 34) and a bristle field (20, 36) mounted thereon. An eccentric (30) is mounted for spinning action on the bristle base plate, positioned in the midst of the bristle field. An eccentric bristle field (38) is mounted on the eccentric. The motion of the brush member produced by a toothbrush drive assembly creates a spinning motion of the eccentric and the eccentric bristle field mounted thereon, resulting in additional oral cleaning action.

4 Claims, 2 Drawing Sheets

(56) References Cited

U.S. PATENT DOCUMENTS

2003/0213076 A1    11/2003    Schutz et al.
2004/0143917 A1*    7/2004    Ek .................................. 15/22.1
2008/0313830 A1    12/2008    Gatzemeyer et al.

FOREIGN PATENT DOCUMENTS

| WO | 03063722 A1 | 8/2003 | |
| WO | WO 2010007358 A2 * | 1/2010 | ............... A46B 7/06 |
| WO | 2010076703 A1 | 7/2010 | |

* cited by examiner

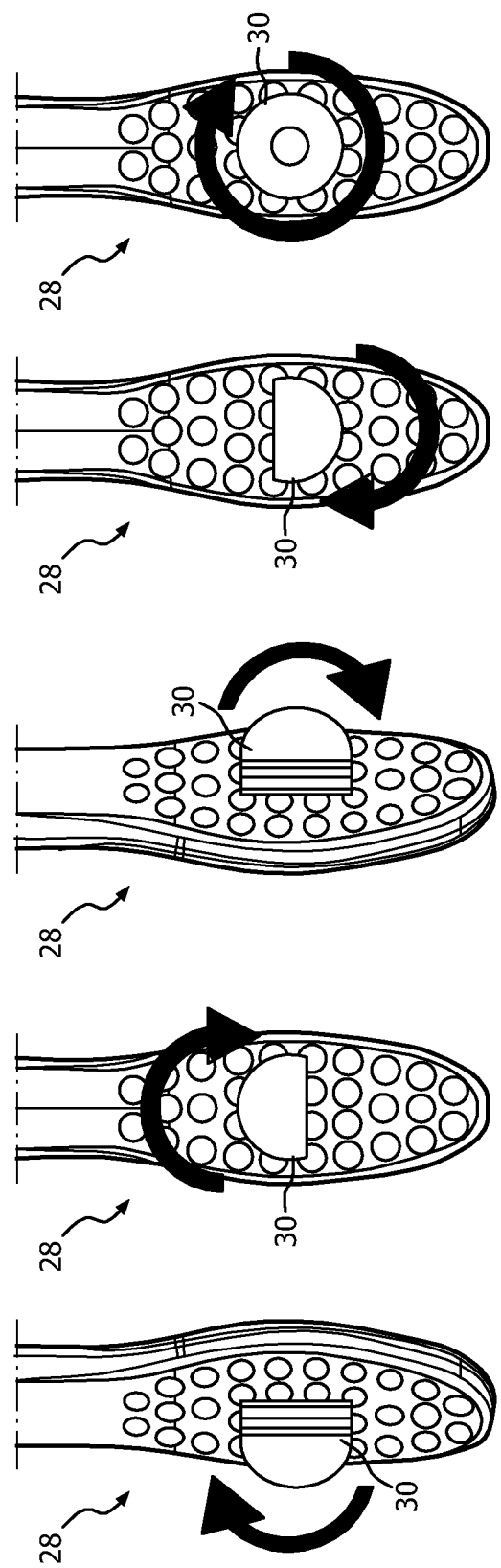

POWER TOOTHBRUSH AND BRUSHHEAD THEREFOR, WITH MULTIPLE MOTION BRUSH MEMBER

REFERENCE TO RELATED APPLICATIONS

This application is a 371 of PCT/IB2011/055387, filed Nov. 30, 2011, which claims the priority of provisional application No. 61/424,743, filed Dec. 20, 2010, the entire contents of which are incorporated herein by reference.

This invention relates generally to power toothbrushes with a brush member having an oscillating motion for cleaning teeth, and more specifically includes such a brush member having multiple simultaneous motions provided by different sections of the brush member.

All power toothbrushes include a brush member which is driven by a drive assembly to produce a brush member motion designed to clean teeth by bristle action. The motion can vary, including rotary and axial motions, as well as a sweeping motion, among others. Typically, the most effective motions are oscillatory, which involve a back-and-forth movement of the brush member through a selected angle. While most power toothbrushes have only a single motion, some power toothbrushes have multiple, typically two, motions, usually a primary motion and a secondary motion, accomplished by two separate parts of the brush member.

In many cases, the secondary motion is a spinning or rotary motion of a tuft field (plurality of tufts) or even a single tuft comprised of a plurality of individual bristles, referred to as a secondary bristle field, separate from the remainder of the brush member bristle field. However, the secondary bristle field portion of the brush member typically is driven by additional mechanical linkages, including the use of cam and gear drives, to create the secondary motion.

Such arrangements typically have significant disadvantages. First, the additional mechanical linkage for the secondary motion has its own separate space requirement, in addition to the space requirement for the primary motion, which increases the overall size of the brushhead assembly and can thus detract from the brushing experience because of the increased size of the brushhead in the mouth. In addition, the linkage operates in frequency ranges of brushhead motion which are noisy and which also result in excessive wear due to high acceleration of the parts. Still further, the additional linkage requires a substantial number of parts and careful assembly work, adding expense to the toothbrush.

Since a multiple motion brush member can have some advantages in oral cleaning, it would be desirable to have a multi-motion toothbrush which can maintain those advantages, while minimizing or eliminating the above-noted disadvantages.

Accordingly, disclosed herein is a power toothbrush and a brushhead for use therewith, the power toothbrush having a handle portion and a drive assembly positioned therein, the brushhead comprising: a neck portion, the proximal end of which is connectable to the handle portion of the toothbrush; a brush member having a bristle base plate and a first bristle field mounted thereto, positioned at a distal end of the neck portion, wherein in operation, the drive assembly moves the brush member and the first bristle field in a selected oscillating or other oral care motion; and an eccentric, mounted for rotation on the bristle base plate, wherein the motion of the brush member imparts a spinning motion to the eccentric and an eccentric bristle field mounted thereon, to assist in the oral care action of the toothbrush.

FIGS. 4A-4E are diagrams of the multiple motion brush member of FIGS. 1-3 which show movement of an eccentric member portion of the brush member in response to a rotary oscillating movement of the brush member.

Figure 1:
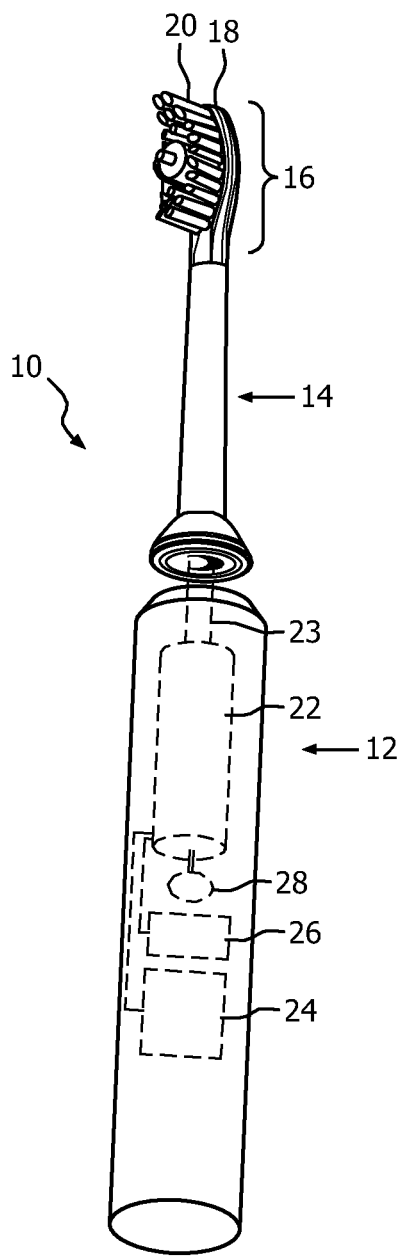
FIG. 1 is a simplified schematic diagram of a power toothbrush with a brushhead assembly and a brush member at the end thereof characterized by multiple motions.

FIG. 1 shows a power toothbrush 10. Toothbrush 10 includes a handle portion 12 and a brushhead assembly 14 which includes a neck portion 15 and at the end thereof a brush member 16 comprising a bristle base member 18 and a field of bristles 20. The brushhead assembly is moved by a drive assembly in the handle, shown generally at 22, with a drive shaft 23 connecting with the brushhead. The drive assembly is powered by a battery 24 which typically is rechargeable, with the toothbrush action being controlled by a microprocessor 26 and an on/off switch 28. As discussed above, the drive assembly can produce various brushhead assembly motions, including the bristle plate and the bristle field mounted thereon, the motions including in particular various oscillating motions, including rotary, axial or sweeping, among others.

In the present invention, the brushhead assembly 16 includes a multi-motion brush member, in particular, a brush member having two different motions. One motion, i.e. the primary motion, is, as described above, produced by the conventional drive assembly in the handle operating on the brushhead assembly and hence the brush member, including the bristle plate and the bristle field mounted thereon. For purposes of explanation herein, the primary motion will be described as oscillating through an angle in the range of 5-20° with a frequency in the range of approximately 200-300 Hz. However, it should be understood that the angle and frequency is by way of illustration only and can be varied significantly in the multi-motion arrangement described below.

Figure 2:
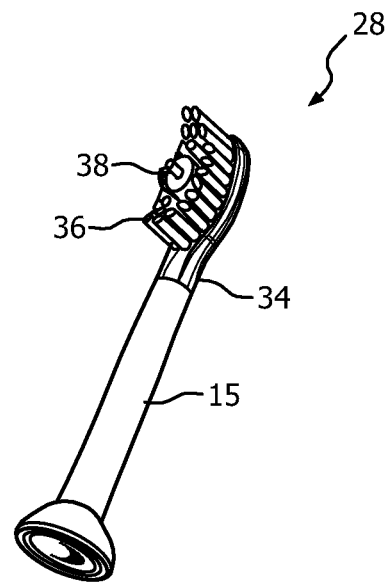
FIG. 2 is a perspective view of the multiple motion brushhead assembly.
Figure 3:
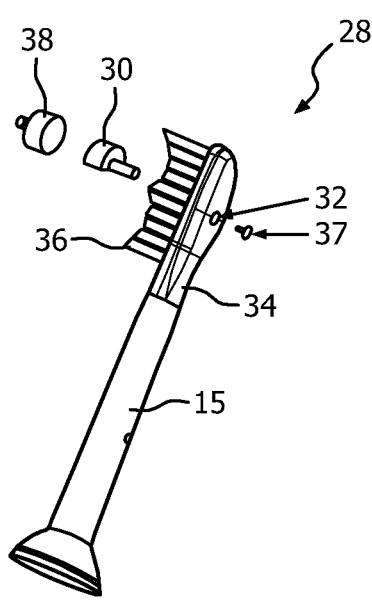
FIG. 3 is an exploded view of FIG. 2.

Referring now to FIGS. 2 and 3, brush member 28 includes an eccentric mass 30. Eccentric mass 30 is rotatably mounted in a bushing 32 which is positioned in the bristle plate 34. A conventional field of bristles 36 is positioned on the bristle plate, with the eccentric 30 in the embodiment shown being located approximately in the center thereof. The eccentric 30 is held to the bristle plate by means of a rivet or similar element 37. Mounted on the eccentric 30 is a bristle field 38 comprised of a single bristle tuft or a small plurality of bristle tufts or other cleaning or polishing member. A single bristle tuft will typically include 20-40 individual bristle filaments, or it could include substantially more bristles, depending upon the diameter of the individual bristle filaments and the diameter of the tuft. Up to 4000 bristle filaments could for instance be used. More than one bristle tuft could also be used, or other cleaning element to accomplish other oral care functions, such as polishing. The bristles or bristle tufts can be attached to the eccentric in various ways, including in-molded, glue or a snap-in arrangement.

In the embodiment shown, the eccentric may have a wide variety of configurations and dimensions. In one example only, the eccentric is a half circle, with a complete circle diameter in the range of 4-12 mm. Many combinations of eccentric geometries and densities can be used to produce an eccentric constant in a desired range. In the embodiment shown, the eccentric constant ($E=m*R$) is within the range of $5 \times 10^{-8}$ to $2 \times 10^{-6}$ kg·m.

In operation, the motion of the brush member 28 (FIGS. 2, 3) will produce a spinning action of the eccentric mass 30 which rotates freely in the bushing 32. FIGS. 4A-4E show a primary oscillating motion of bristle member 28 and the resulting motion of eccentric 30. This motion illustrates an arrangement where the motion of the eccentric is in phase with the brush member rotation. When the two are not in phase, the position of the eccentric relative to the motion of the brush member will be different than that shown, although the eccentric will still spin in only one direction as the brush member oscillates.

As the brush member 28 rotates to one end of its range of motion from a neutral or rest position, eccentric 30 will begin rotating/spinning in one direction (FIG. 4A) to the position shown. As brush member 28 rotates back to its original rest position, eccentric 30 will rotate approximately 90° (FIG. 4B). Rotation of bristle member 28 to the other end of its range of motion results in a further 90° rotation of the eccentric in the same direction (FIG. 4C). Movement of brush member 28 back to its original rest position results in continued movement of the eccentric 90° in the same direction (FIG. 4D). As shown in FIG. 4E, as brush member 28 oscillates back and forth, the eccentric and its associated bristle field will continue to spin (rotate) in one direction only.

This produces an additional cleaning effect or other oral care effect, such as polishing, on the teeth, and can reach, for instance, the interproximal area, depending on the height of the bristles on the eccentric. Typically, the bristle field on the eccentric will be high enough to make contact with the teeth. The exact height of the eccentric bristles relative to the bristle field on the brush member can be varied depending upon the additional desired oral care action.

In operation, the spinning action of the eccentric will not affect the oscillating action, including the frequency, of brush member 28. The frequency of the brush member will determine to some extent the frequency of the eccentric, depending upon the particular design of the eccentric. For a brush member frequency of 260 Hz, for instance, an eccentric arrangement as discussed above will result in a spinning frequency of the eccentric and the bristle field 38 of between 50-100 Hz.

The advantage of the above arrangement is that a multi-motion bristle action is achieved without any special linkages or cams for the additional secondary motion, thereby overcoming the noted disadvantages of prior multi-motion toothbrushes.

Although a preferred embodiment has been disclosed for purposes of illustration, it should be understood that various changes and modifications and substitutions could be made in the preferred embodiment without departing from the spirit of the invention as defined by the claims which follow:

The invention claimed is:
1. A power toothbrush, comprising:
a handle portion (12);
a drive assembly (22) positioned within the handle; and
a brushhead (14) which includes a neck portion (15), the proximal end of which is connectable to the handle portion of the toothbrush;
a brush member (16, 28) having a bristle base plate (18, 34) and a first bristle field (20, 36) mounted thereto, positioned at a distal end of the neck portion, wherein in operation, the drive assembly moves the brush member and the first bristle field in an oscillating motion about the longitudinal axis of the neck portion; and
an eccentric (30), mounted for rotation on the bristle base plate, wherein the motion of the brush member imparts a spinning motion to the eccentric and an eccentric bristle field (38) mounted thereon, to assist in oral care action of the toothbrush.

2. The power toothbrush of claim 1, wherein the eccentric is mounted in the midst of the first bristle field.

3. The power toothbrush of claim 1, wherein the eccentric is in the form of a half circle, with a diameter in the range of 5-14 mm.

4. The power toothbrush of claim 1, wherein the eccentric has an eccentric constant in the range of $5\times10^{-8}$ to $2\times10^{-6}$.

\* \* \* \* \*